United States Patent [19]

Trundle

[11] Patent Number: 4,861,899
[45] Date of Patent: Aug. 29, 1989

[54] PHOTOCHROMIC GAMMA BUTYROLACTONES

[75] Inventor: Clive Trundle, Towcester, United Kingdom

[73] Assignee: The Plessey Company plc., United Kingdom

[21] Appl. No.: 57,144

[22] Filed: Jun. 3, 1987

[30] Foreign Application Priority Data

Jun. 3, 1987 [GB] United Kingdom ............ 8613420

[51] Int. Cl.$^4$ .................................... C07D 233/56
[52] U.S. Cl. ............................. 549/58; 549/60; 549/320
[58] Field of Search ............... 549/58, 60, 320

[56] References Cited

U.S. PATENT DOCUMENTS

| | | | |
|---|---|---|---|
| 4,145,536 | 3/1979 | Heller | 548/451 |
| 4,220,708 | 9/1980 | Heller | 549/60 |
| 4,685,783 | 8/1987 | Heller et al. | 549/60 |

OTHER PUBLICATIONS

Chemical Abstracts, vol. 91, No. 3, Abstract 20213d, Jul. 16, 1979.
Trundle, "Substituent Effects on Photochromic Fulgides", 1980.

*Primary Examiner*—Mary C. Lee
*Assistant Examiner*—Zinna Northington
*Attorney, Agent, or Firm*—Sughrue, Mion, Zinn, Macpeak & Seas

[57] ABSTRACT

The invention relates to a photochromic gamma butyrolactone having the general formula (I):

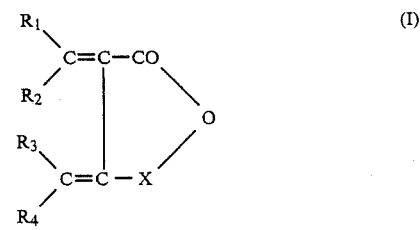

in which X represents $>CH_2$ or $>C(CH_3)_2$; $R_1$, $R_2$ and $R_4$ independently represent a group selected from hydrogen, alkyl or aryl (including substituted aryl), with the proviso that one of $R_1$ and $R_2$ is always hydrogen, and $R_3$ is a 3-thienyl, 3-furyl, 3-benzothienyl or 3-benzofuryl group in which the 2-position is substituted with an alkyl, aralkyl or aryl group (including substituted aryl).

The lactones are useful in photolithography and in the production of security inks and markings and in the production of data recording materials.

4 Claims, No Drawings

PHOTOCHROMIC GAMMA BUTYROLACTONES

This invention relates to a series of photochromic compounds which are based on bis-methylene-γ-butyrolactone.

BACKGROUND OF THE INVENTION

British Pat. No. 2167744 describes a series of gamma lactones having the general formula:

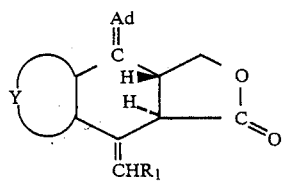

in which Ad=C< represents an adamantylidene group, $R_1$ is selected from hydrogen, alkyl and aryl and

represents a carboxylic or heterocyclic group, such as furyl or thienyl. The utility of the gamma lactones described in the above patent specification is as antitumoural compounds or as intermediates for producing compounds having such pharmacological activity.

We have now discovered that structurally related lactones have valuable photochromic properties.

SUMMARY OF THE INVENTION

According to the present invention there is provided a photochromic gamma butyrolactone having the general formula (I):

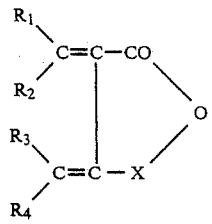

in which X represents >$CH_2$ or >$C(C_3)_2$; $R_1$, $R_2$ and $R_4$ independently represent a group selected from hydrogen, alkyl, aralkyl or aryl (including substituted aryl), with the proviso that one of $R_1$ and $R_2$ is always hydrogen, and $R_3$ is a 3-thienyl, 3-furyl, 3-benzothienyl or 3-benzofuryl group in which the 2-position is substituted with an alkyl, aralkyl or aryl group (including substituted aryl). The 5-position of the thienyl or furyl ring may also be substituted e.g. with an alkyl, aryl or aralkyl group.

Compounds of the general formula (I) have the ability to undergo reversible ring closure to a coloured form, the ring closure being induced either thermally or by irradiation with light in the U.V. region or by a combination of both heating and irradiation. Heating alone to temperatures in the region of 100° C. will generally bring about ring closure. The coloured form can be produced by irradiation with U.V. light at lower temperatures, e.g. ambient.

DETAILED DESCRIPTION OF THE INVENTION

The formation of the coloured state is illustrated by the following equation which shows the photocyclisation of a 3-thienyl or 3-furyl butyrolactone:

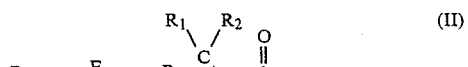

(Bleached state)

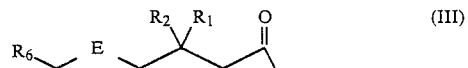

(Coloured state)

In the above formulae (II) and (III), $R_1$, $R_2$, $R_5$, $R_4$, $R_6$ and X have the same significance as in formula (I) and E represents oxygen or sulphur.

Preferred gamma butyrolactones are those having the general formulae (4) or (5) below

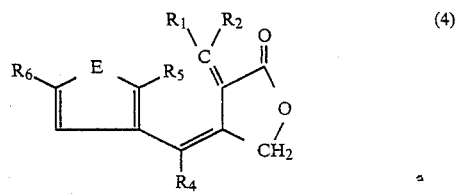

or

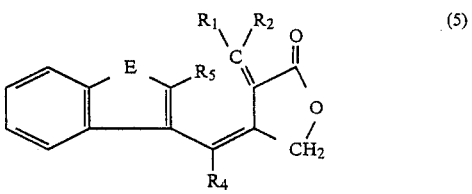

wherein E represents oxygen or sulphur, $R_1$, $R_2$, $R_4$, and $R_6$ are independently selected from hydrogen, lower alkyl and aryl, and $R_5$ is alkyl or aryl, with the proviso that one of $R_1$ and $R_2$ is always hydrogen.

The thermally or U.V. induced ring closure occurs by ring closures onto the 2-position of the thienyl or furyl ring and does not involve the formation of radicals or reactive intermediates. Reversal is effected by irradiation with light at about 440 nm wavelength. Typically, the coloured compounds are bleached by irradiation with a laser of 436 nm wavelength. The compounds of the invention are very resistant to fatigue reactions leading to formation of irreversible products. This is achieved by blocking the only significant fatigue process, a 1,5 hydrogen shift, by introducing a nonhydrogen substituent $R^1$ in the 2-position. As a consequence, there is a virtual absence of fatigue reactions and the compounds are capable of undergoing a very large number of colour change cycles.

The coloured form of compounds of this invention are generally yellow to red, the precise absorption characteristics depending on the substituents in the furan or thiophene ring or whether this is benzannelated.

Compounds in which one of $R_1$ and $R_2$ is hydrogen have the advantage that ring closure can be effected by heating, generally to a temperature of about 100° C. or less. For example, such compounds can be converted to their coloured form by heating in refluxing toluene. In this manner, substantially 100% of the lactone is converted to the coloured form, whereas irradiation with U.V. light generally achieves a maximum of about 60% conversion. This property is of particular value in the contrast enhancement of photolithographic images e.g. as described in our co-pending U.K. patent application No. 8707015 and in our PCT patent application No. PCT/GB87/00275. As described in our above co-pending application, a coloured layer of a lactone of the above general formula can be coated onto a photoresist and exposed through an imaging negative using light of a wavelength which bleaches the coloured form of the lactone. Since the lactones of the present invention are bleached by radiation of a wavelength which is commonly used to expose photoresists, an in situ mask is formed on the photoresist during the photoresist exposure step.

Other uses of the compounds of this invention include use in security inks or markings (in which the coloured form can, for example, be made visible by heating or U.V. irradiation), or in data recording materials or as a component in colour image generation by laser writing.

The lactones of the present invention can be prepared in a first stage by condensing a ketone of formula (IVA) of (IVB) below with a diester of a succinic acid of formula (V) below using a Stobbe condensation:

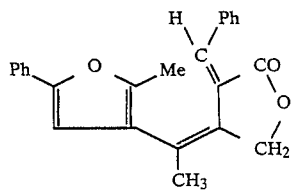

(IVA)

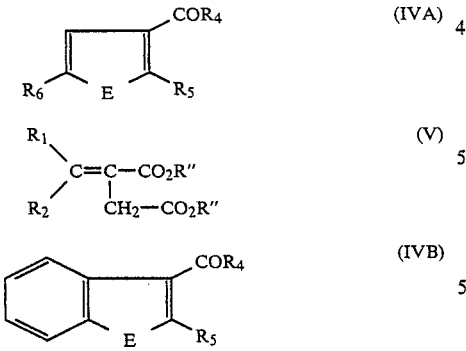

where R" is an alkyl residue, preferably a lower alkyl ester, e.g. methyl, ethyl, propyl or butyl.

The reaction of ketones and succinic acid diesters by the Stobbe condensation is described in detail in U.S. Pat. No. 4,220,708, the disclosure of which is specifically incorporated herein.

In the next stage of the synthesis, the resultant acid ester is reduced to an acid alcohol by a suitable reducing agent, e.g. Super hydride (lithium triethylborohydride) or methyl lithium, followed by dehydration e.g. by heating with a suitable catalyst such as p-toluene sulphonic acid to yield the lactone.

The following Example illustrates the preparation of lactones in accordance with the invention.

EXAMPLE

2-Methyl-3-acetyl-5-phenylfuran (40 g) and diethyl E-benzylidene succinate (55 g) in toluene was added dropwise to a suspension of sodium hydride (50% suspension in oil) (20 g) in toluene. The reaction was maintained at room temperature and stirred for 12 hours. The resultant solution was poured onto ice and the sodium salt of the acid ester extracted with water. The aqueous extract was acidified (5M HCl) and extracted with ether. The ether layer was dried and evaporated to give crude acid ester (30 g).

To the resulting acid ester (8 grms) in tetrahydrofuran was added superhydride (100 cm³ 0.1M solution in THF) and the solution refluxed (8 hours) and left to cool overnight. The solution obtained was poured onto ice and the THF evaporated. The residue was acidified with iced HCl and extracted with ether. The ethereal solution of acid alcohol was dehydrated by heating with p-toluene sulphonic acid and the lactone (2 g) having the structural formula below was separated from the reaction mixture by chromatography (alumina (neutral)/chloroform).

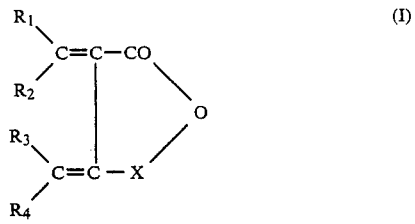

I claim:

1. A photochromic gamma butyrolactone having the general formula (I):

$$R_1 \atop R_2 \!\!>\!\! C\!=\!C\!-\!CO \atop R_3 \atop R_4 \!\!>\!\! C\!=\!C\!-\!X \!\!\!\!\!\!\!\!\!\!\!\!\!\! O \quad (I)$$

wherein X represents $>CH_2$ or $>C(CH_3)_2$; $R_1$, $R_2$ and $R_4$ independently represent a group selected from hydrogen, alkyl or aryl with the proviso that one of $R_1$ or $R_2$ is always hydrogen, and $R_3$ is a 3-thienyl, 3-furyl, 3-benzothienyl or 3-benzofuryl group in which the 2-position is substituted with an alkyl, aralkyl or aryl group and wherein said alkyl groups have from 1 to 20 carbon atoms, said aryl groups have 6 to 14 carbon atoms and said aralkyl groups have 7 to 12 carbon atoms.

2. A photochromic lactone according to claim 1 in which $R_1$, $R_2$ and $R_4$ independently represent hydrogen, an alkyl group having 1 to 5 carbon atoms or phenyl.

3. A photochromic lactone according to claim 2 in which $R_3$ is a 3-thienyl or 3-furyl group having a lower alkyl or phenyl substituent in the 5-position.

4. A photochromic gamma butyrolactone having the general formula:
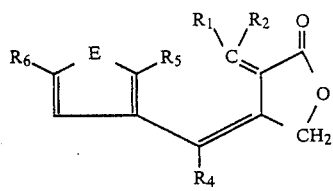 (4)
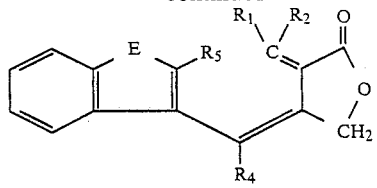 (5)
wherein E represents oxygen or sulphur; $R_1$, $R_2$, $R_4$ and $R_6$ are independently selected from hydrogen, alkyl and aryl, and $R_5$ is alkyl or aryl, with the proviso that one of $R_1$ or $R_2$ is always hydrogen, and wherein said alkyl groups contain 1 to 18 carbon atoms and said aryl groups are phenyl or naphthyl.
* * * * *